United States Patent
McIntire et al.

(10) Patent No.: US 7,819,710 B2
(45) Date of Patent: Oct. 26, 2010

(54) TERMINATION CAP FOR TERMINATING AN ELECTRICAL LEAD DIRECTLY TO A STUD OF AN ELECTRODE AND AN ELECTRODE LEAD ASSEMBLY CONTAINING SUCH TERMINATION CAP

(75) Inventors: James F. McIntire, West Linn, OR (US); Brian Erik Haug, Portland, OR (US)

(73) Assignee: Tyco Electronics Corporation, Berwyn, PA (US)

( * ) Notice: Subject to any disclaimer, the term of this patent is extended or adjusted under 35 U.S.C. 154(b) by 0 days.

(21) Appl. No.: 12/236,303

(22) Filed: Sep. 23, 2008

(65) Prior Publication Data

US 2010/0075549 A1     Mar. 25, 2010

(51) Int. Cl.
*H01R 9/24* (2006.01)
(52) U.S. Cl. .................................................. 439/890
(58) Field of Classification Search .............. 439/859, 439/592, 17, 20, 890; 600/391, 392, 394; 403/90
See application file for complete search history.

(56) References Cited

U.S. PATENT DOCUMENTS

| | | | |
|---|---|---|---|
| 3,069,753 A | 12/1962 | Lalmond et al. | |
| 3,325,769 A | 6/1967 | Travis | |
| 3,353,141 A | 11/1967 | Budai | |
| 3,462,542 A | 8/1969 | Richter | |
| 3,513,045 A | 5/1970 | Emmel et al. | |
| 3,599,629 A | 8/1971 | Gordy | |
| 3,641,482 A | 2/1972 | Bretting | |
| 3,670,290 A | 6/1972 | Angele et al. | |
| 3,696,319 A | 10/1972 | Olsson | |
| 3,802,974 A | 4/1974 | Emmel | |
| 4,112,941 A * | 9/1978 | Larimore | 600/394 |
| 4,331,153 A * | 5/1982 | Healy | 600/392 |
| 4,350,165 A | 9/1982 | Striese | |
| 4,353,372 A | 10/1982 | Ayer | |
| 4,357,750 A | 11/1982 | Ostman | |
| 4,438,999 A | 3/1984 | Lang | |
| 4,490,005 A * | 12/1984 | Hovey | 439/592 |
| 4,573,752 A | 3/1986 | Rich | |
| 4,653,501 A | 3/1987 | Cartmell et al. | |
| 4,686,995 A | 8/1987 | Fournial et al. | |
| 4,757,817 A * | 7/1988 | Healy | 600/392 |
| 4,945,911 A * | 8/1990 | Cohen et al. | 600/391 |
| 5,232,383 A * | 8/1993 | Barnick | 439/859 |
| 5,235,132 A | 8/1993 | Ainsworth et al. | |
| 5,250,127 A | 10/1993 | Hara | |
| 5,897,406 A * | 4/1999 | Benes et al. | 439/859 |
| 5,978,693 A | 11/1999 | Hamilton et al. | |
| 6,071,141 A | 6/2000 | Semmeling et al. | |

(Continued)

FOREIGN PATENT DOCUMENTS

EP     1264575 A2    12/2002

*Primary Examiner*—Chandrika Prasad

(57) ABSTRACT

A termination cap is provided for terminating an electrical lead to a stud of an electrode. The termination cap includes a body and a receptacle extending into the body. The receptacle includes a size and shape that is complimentary to the stud of the electrode such that the receptacle is configured to receive at least a portion of the stud therein. The receptacle is configured such that when the stud is received within the receptacle, the receptacle is configured to hold a portion of the electrical lead between the body and the stud such that the electrical lead is engaged with and electrically connected to the stud.

20 Claims, 4 Drawing Sheets

U.S. PATENT DOCUMENTS

| | | |
|---|---|---|
| 6,659,794 B2 | 12/2003 | Yamatani et al. |
| 6,672,788 B2 * | 1/2004 | Hathaway .................... 403/90 |
| 6,705,899 B1 | 3/2004 | Ji |
| 6,847,836 B1 | 1/2005 | Sujdak |
| 7,001,207 B2 | 2/2006 | Boemmel et al. |
| 7,062,309 B2 | 6/2006 | Ryu et al. |
| 7,172,455 B2 | 2/2007 | Pabst et al. |
| 2005/0251004 A1 | 11/2005 | Istvan et al. |

* cited by examiner

TERMINATION CAP FOR TERMINATING AN ELECTRICAL LEAD DIRECTLY TO A STUD OF AN ELECTRODE AND AN ELECTRODE LEAD ASSEMBLY CONTAINING SUCH TERMINATION CAP

BACKGROUND OF THE INVENTION

The subject matter described and illustrated herein relates generally to electrode lead assemblies, and more particularly, to a termination cap for terminating an electrical lead to an electrode.

An electrocardiograph (ECG) system monitors heart electrical activity in a patient. Conventional ECG systems utilize electrodes placed on a patient in specific locations to detect electrical impulses generated by the heart during each beat. Typically, the electrical impulses or signals are detected by and directly transferred from the electrodes to a stationary ECG monitor via multiple cables or wires. The ECG monitor performs various signal processing and computational operations to convert the raw electrical signals into meaningful information that can be displayed on a monitor or printed out for review by a physician.

ECG measurements are taken by applying electrodes to different chest locations and additional body locations, such as the arms and legs. Each of the electrodes is electrically connected to the ECG monitor by a corresponding electrical lead. To electrically connect the electrical leads to the electrodes, an end portion of each electrical lead typically includes an electrical connector that engages an electrical contact, for example a stud, of the corresponding electrode. Each electrical connector is typically connected, or terminated, to the corresponding lead using conventional termination methods, such as by welding, soldering, or crimping the electrical connector to the end portion of the corresponding electrical lead. However, terminating the electrical connectors to the electrical leads may increase the cost and/or difficulty of manufacturing and/or assembling the electrical leads. Moreover, the electrical connectors typically engage the electrical contacts of the electrodes using a "snap", "pinch", or "grabber" arrangement, which may increase a size and/or a complexity of the electrical leads and therefore may increase the cost and/or difficulty of manufacturing the electrical leads, assembling the electrical leads, and/or terminating the electrical leads to the electrodes.

There is a need for an electrical lead that is less costly and/or more easily manufactured, assembled, and/or terminated to an electrode than at least some known electrical leads.

BRIEF DESCRIPTION OF THE INVENTION

In one embodiment, a termination cap is provided for terminating an electrical lead to a stud of an electrode. The termination cap includes a body and a receptacle extending into the body. The receptacle includes a size and shape that is complimentary to the stud of the electrode such that the receptacle is configured to receive at least a portion of the stud therein. The receptacle is configured such that when the stud is received within the receptacle, the receptacle is configured to hold a portion of the electrical lead between the body and the stud such that the electrical lead is engaged with and electrically connected to the stud.

In another embodiment, an electrode lead assembly is provided. The electrode lead assembly includes a termination cap including a body and a receptacle extending into the body, and an electrode comprising a stud. At least a portion of the stud is received within the receptacle. The electrode lead assembly also includes an electrical lead. A portion of the electrical lead extends within the receptacle between the stud and the body of the termination cap such that the electrical lead is engaged with and electrically connected to the stud.

In another embodiment, an electrical lead assembly is provided for termination to a stud of an electrode. The electrical lead assembly includes an electrical lead, and a termination cap including a body and a receptacle extending into the body. The receptacle includes a size and shape that is complimentary to the stud of the electrode such that the receptacle is configured to receive at least a portion of the stud therein. The receptacle is configured such that when the stud is received within the receptacle, the receptacle is configured to hold a portion of the electrical lead between the body and the stud such that the electrical lead is engaged with and electrically connected to the stud.

BRIEF DESCRIPTION OF THE DRAWINGS

FIG. 6 is a schematic diagram of an exemplary embodiment of an electrocardiogram (ECG) system that the electrode lead set shown in FIG. 1 may be used with.

DETAILED DESCRIPTION OF THE INVENTION

Figure 1:
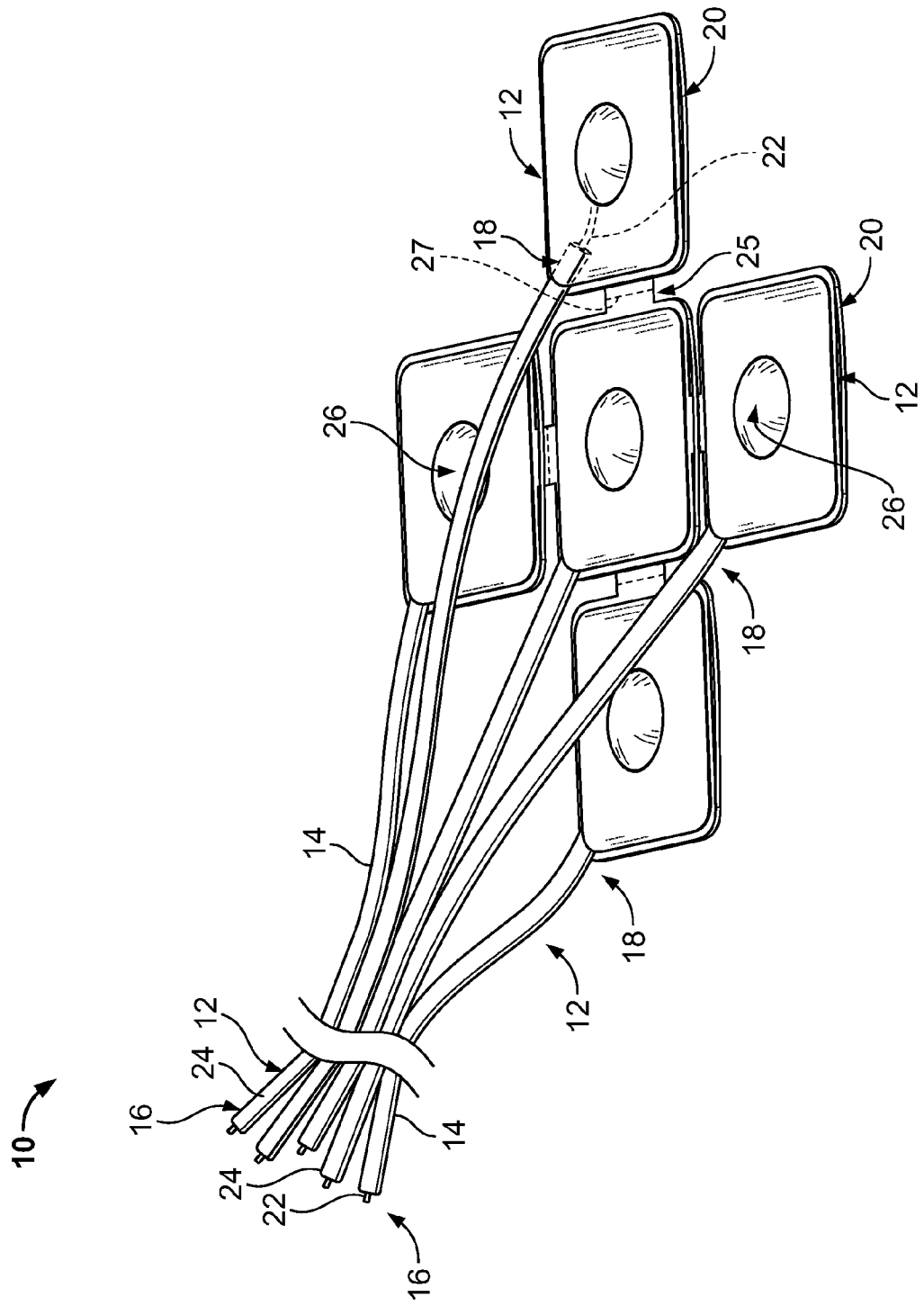
FIG. 1 is a perspective view of an exemplary embodiment of an electrode lead set for electrical connection to a patient's body.

FIG. 1 is a perspective view of an exemplary embodiment of an electrode lead set 10 for electrical connection to a patient's body. The electrode lead set 10 includes a plurality of electrode lead assemblies 12. Each electrode lead assembly 12 includes an electrical lead 14 that extends along a length from a proximal end portion 16 to a distal end portion 18. The distal end portion 18 of each of the electrical leads 14 includes an electrode 20. Specifically, and as will be described in more detail below, each electrode 20 is electrically connected to the corresponding electrical lead 14 at the distal end portion 18 thereof. The electrodes 20 are each configured to be placed at different locations on the patient's body for measuring physiological information of the patient's body. As will be described in more detail below, termination caps 26 are provided for terminating the electrical leads 14 to the corresponding electrodes 20.

Each electrical lead 14 includes an electrical conductor 22 that extends along the length of the electrical lead 14 between the proximal and distal end portions 16 and 18, respectively. Each of the electrical conductors 22 is electrically connected to the corresponding electrode 20 to provide an electrical connection between the electrode 20 and any electronic device, for example any electronic device that reads and/or delivers electrical signals from and/or to a body, such as, but not limited to, a monitoring device (such as, but not limited to, an electrocardiogram (ECG) monitoring device (e.g., the ECG monitoring device 102 shown in FIG. 6), a hand-held system monitor (not shown), and/or the like), a stimulating device, and/or the like. Specifically, at the proximal end portion 16 of each of the electrical leads 14, the electrical conductor 22 is electrically connected to the electronic device (whether directly or indirectly using an extension, one or more electrical connectors, and/or the like) such that each of the electrodes 20 are electrically connected to one or more corresponding circuits (not shown) of the electronic device. The electronic device may be any suitable processing device that is capable of performing signal processing and computational operations to convert the raw electrical signals from and/or to the electrodes 20 into meaningful information (such as, but not limited to, ECG information and/or the like) that may optionally be displayed on a monitor (e.g., the monitor 104 shown in FIG. 6), printed for review by a physician, and/or the like.

In the exemplary embodiment, each of the electrical leads 14 includes the electrical conductor 22 and an electrically insulative cover 24. In other embodiments, each of the electrical leads 14 may be shielded along at least a portion of the length of the electrical lead 14. The electrical leads 14 may be shielded using any suitable arrangement, configuration, structure, means, and/or the like, such as, but not limited to, surrounding at least a portion of the electrical conductors 22 with any suitable electrically insulative material(s) (not shown), and surrounding at least a portion of the insulative material with an electrically conductive material (not shown) that is at least partially surrounded by the electrically insulative cover 24.

The electrical conductors 22 may each be fabricated from any suitable electrically conductive material(s) that enables the electrical conductors 22 to electrically connect the electrodes 20 to the electronic device and/or that enables the electrode lead set 10 to function as described herein, such as, but not limited to, silver, aluminum, gold, copper, other metallic conductors, non-metallic conductors (such as, but not limited to, carbon and/or the like), and/or the like. The electrical conductors 22 may also have any suitable configuration, shape, and/or the like that that enables the electrical conductors 22 to electrically connect the electrodes 20 to the electronic device and/or that enables the electrode lead set 10 to function as described herein, such as, but not limited to, an approximately cylindrical wire (whether the wire consists of a plurality of strands or only one strand), an approximately planar shape, and/or the like. The insulative cover 24 may be fabricated from any suitable insulative material(s) that facilitates insulating the electrical conductors 22 and/or that enables the electrode lead set 10 to function as described herein, such as, but not limited to, polyester (e.g., Mylar®), polyvinyl chloride, thermo-plastic-elastomer, and/or polyimide (e.g., Kapton®).

The electrode lead set 10 may include any number of electrode lead assemblies 12 for positioning any number of electrodes 20 at any number of locations on the patient's body. In the exemplary embodiment of FIGS. 1 and 6, the electrode lead set 10 includes five electrode lead assemblies 12 for use within an ECG system (e.g., the ECG system 100 shown in FIG. 6). For example, the electrodes 20 of four of the five electrode lead assemblies 12 are configured to be placed at different limbs of a patient's body (e.g., both arms and both legs) and one of the five electrode lead assemblies 12 is configured to be placed on the chest region of the patient's body. An example of an alternative embodiment of the electrode lead set 10 includes only three electrode lead assemblies 12 for use within an ECG system, wherein the electrodes 20 of the three electrode lead assemblies 12 are configured to be placed at different limbs of the patient's body (e.g., both arms and the left leg). Yet another example of an alternative embodiment of the electrode lead set 10 includes ten electrode lead assemblies 12 wherein the electrodes 20 of six of the electrode lead assemblies 12 are configured to be placed at six different locations on a chest region of the patient's body (e.g., the prescribed ECG precordial locations $V_1$, $V_2$, $V_3$, $V_4$, $V_5$, and $V_6$ of the American Heart Association (AHA) or the prescribed ECG precordial locations $C_1$, $C_2$, $C_3$, $C_4$, $C_5$, and $C_6$ of the International Electrotechnical Commission (IEC)) and the electrodes 20 of four electrode lead assemblies 12 are configured to be placed on different limbs of the patient's body (e.g., the prescribed locations RA, LA, RL, and LL of the AHA or the prescribed locations R, L, N, and F of the IEC). Even another example of an alternative embodiment of the electrode lead set 10 includes twelve electrode lead assemblies 12 for use within an ECG system, wherein some of the electrodes 20 of the twelve electrode lead assemblies 12 are configured to be placed at different limbs of the patient's body and some of the electrodes 20 of the twelve electrode lead assemblies 12 are configured to be placed on the chest region of the patient's body. The electrode lead set 10 is not limited to the three, five, ten, and twelve electrode lead assembly 12 embodiments described and/or illustrated herein, but rather may include any number of electrode lead assemblies 12 for positioning any number of electrodes 20 at any number of locations on the patient's body.

In some embodiments, the electrodes 20 may be held in an array when not in use. The array may have any pattern, whether random, ordered, or a combination of random and ordered. In the exemplary embodiment, the electrodes 20 are held in the array shown in FIG. 1 via a base 25 that is connected to and common with each of the electrodes 20. The base 25 includes a separable interface 27 between adjacent electrodes 20. The base 25 may include any suitable configuration, arrangement, structure, means, and/or the like that enables the base 25 to hold the electrodes 20 in the array, such as, but not limited to, a sheet that is removably attached to each of the electrodes 20. The separable interface 27 may include any suitable configuration, arrangement, structure, means, and/or the like that enables the separable interface to hold the electrodes 20 in the array, such as, but not limited to, perforated tape and/or perforations of any suitable size, shape, spacing, and/or frequency. The electrodes 20 may alternatively be maintained in the array using any other suitable structure, means, and/or the like, such as, but not limited to, adhesive, a band (not shown) surrounding at least a portion of the electrodes 20 and/or surrounding a portion of each of the electrical leads 14, a base (not shown) connected to and common with a portion of each of the electrical leads 14, a separable interface (not shown) between at least a portion of each of the electrical leads 14, and/or the like.

Figure 2:
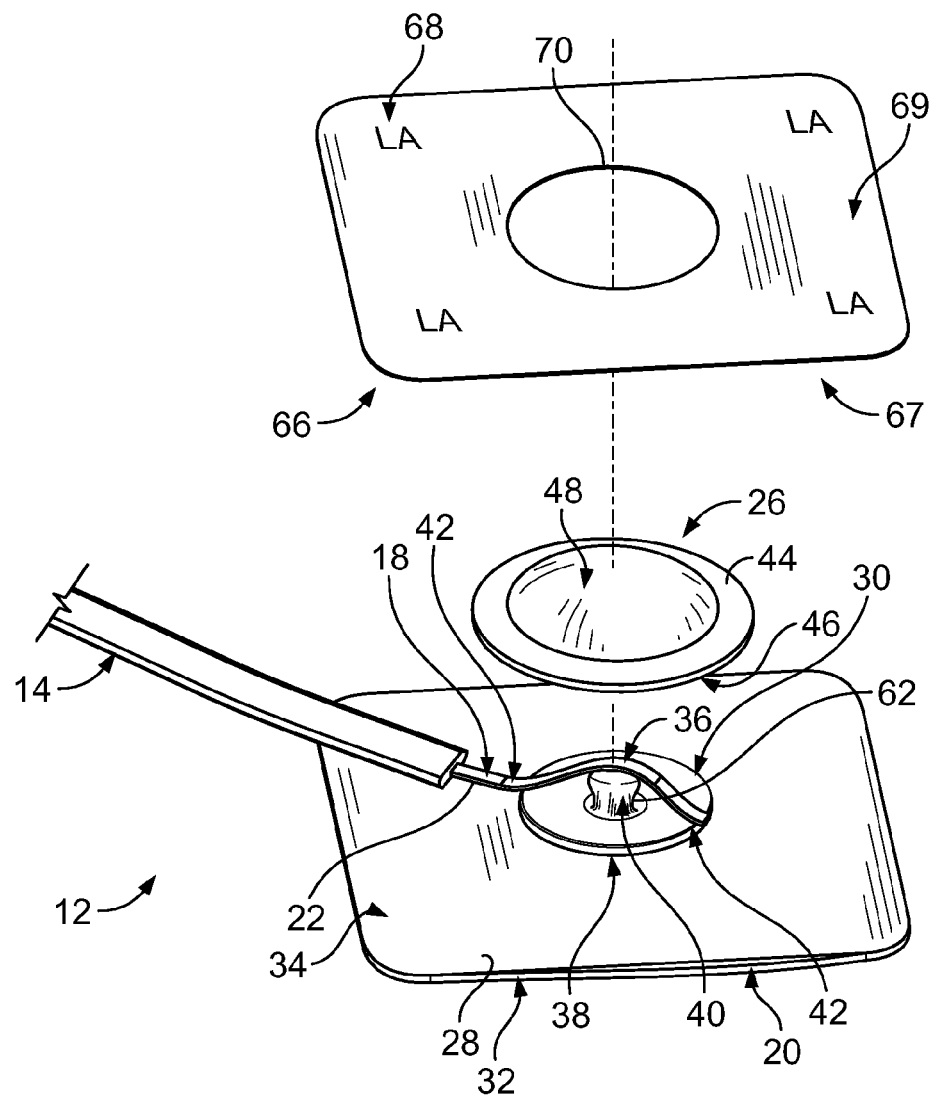
FIG. 2 is a partially exploded perspective view of a portion of an exemplary embodiment of an electrode lead assembly of the electrode lead set shown in FIG. 1.
Figure 3:
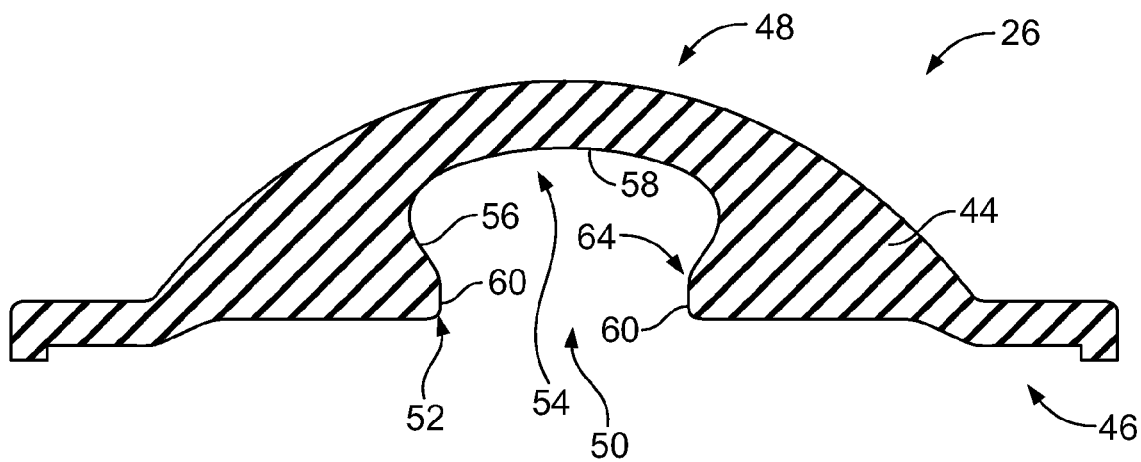
FIG. 3 is a cross-sectional view of an exemplary embodiment of a termination cap of the electrode lead assembly shown in FIG. 2.

FIG. 2 is a partially exploded perspective view of a portion of an exemplary embodiment of an electrode lead assembly 12 of the electrode lead set 10 (FIG. 1). FIG. 3 is a cross-sectional view of an exemplary embodiment of a termination cap 26 of the electrode lead assembly 12 (FIGS. 1 and 2). Each electrode lead assembly 12 includes the electrical lead 14, the electrode 20, and the termination cap 26. A combination of an electrical lead 14 and a termination cap 26 may be referred to herein as an "electrical lead assembly". A combination of an electrical lead 14, an electrode 20, and a termination cap 26 may be referred to herein as an "electrode lead assembly".

The electrode 20 may be any suitable type of electrode that enables the electrode 20 to function as described herein. In the exemplary embodiment, the electrode 20 is a known ECG electrode. For example, the electrode 20 includes a base 28 that holds an electrical contact 30. The base 28 includes a side portion 32 that engages the patient's body and an opposite side portion 34. The electrical contact 30 extends between opposite end portions 36 and 38. As will be described in more detail below, the end portion 36 electrically connects to the electrical conductor 22 of the electrical lead 14. In some embodiments, a portion of the end portion 38 of the electrical contact 30 extends on the side portion 32 of the base 28 and engages the patient's body to form an electrical connection between the electrical contact 30 and the patient's body. In other embodiments, the end portion 38 of the electrical contact 30 engages another electrical contact (not shown) that extends on the side portion 32 of the base 28 for electrical connection to the patient's body. In still other embodiments, the base 28 of the electrode 20 holds an electrically conductive fluid, adhesive, gel, and/or the like (not shown) that is exposed on the side portion 32 of the base 28 for electrical connection with the patient's body; and the end portion 38 of the electrical contact 30 engages the electrically conductive fluid, adhesive, gel, and/or the like to form an electrical connection between the electrical contact 30 and the electrically conductive fluid, adhesive, gel, and/or the like. The end portion 36 of the electrical contact 30 may have any suitable size and/or shape that enables the electrode 20 to function as described herein and/or that enables the termination cap 26 to function as described herein. In the exemplary embodiment, the end portion 36 of the electrical contact 30 includes a stud 40 such that the electrical contact 30 is a conventional snap-fit contact. As used herein, the term "stud" is intended to mean a protrusion.

The termination cap 26 terminates the distal end portion 18 of the electrical lead 14 to the electrode 20. Specifically, and as will be described below, the termination cap 26 terminates an end portion 42 of the electrical conductor 22 to the electrical contact 30 of the electrode 20. The termination cap 26 includes a body 44 having opposite side portions 46 and 48. When the termination cap 26 is assembled on the electrode 20, the side portion 46 faces the base 28 of the electrode 20. Although shown as generally circular, the body 44 of the termination cap 26 may have any shape. The termination cap 26 includes a receptacle 50 that extends into the body 44 on the side portion 46 thereof. In the exemplary embodiment, the receptacle 50 extends into the body 44 between an open end portion 52 and a bottom end portion 54. Specifically, the receptacle 50 is defined by a side wall 56 that extends from the open end portion 52 and the bottom end portion 54. The bottom end portion 54 includes a bottom wall 58 that intersects the side wall 56. The receptacle 50 has a size and shape that is complimentary to the electrical contact 30 of the electrode 20 such that the receptacle 50 is configured to receive at least a portion of the end portion 36 of the electrical contact 30 therein. As will be described in more detail below, the receptacle 50 is configured such that when the electrical contact 30 is received within the receptacle 50, the receptacle 50 holds at least a portion of the end portion 42 of the electrical conductor 22 therein such that the end portion 42 of the electrical conductor 22 is engaged with and electrically connected to the end portion 36 of the electrical contact 30. Alternatively, the receptacle extends completely through the body 44 such that the body 26 does not include the bottom wall 58 or includes only a portion of the bottom wall.

The receptacle 50 is not limited to the size and shape described and illustrated in the exemplary embodiment. Rather, the receptacle 50 may have any suitable size and shape, depending on the size and shape of the electrical contact 30, that enables the receptacle 50 to receive at least a portion of the electrical contact 30 and hold at least a portion of the end portion 42 of the electrical conductor 22 in electrical connection with the end portion 36 of the electrical contact 30. In the exemplary embodiment, the receptacle 50 has a size and shape that is configured to connect to the stud 40 of a conventional snap-fit electrical contact. Accordingly, in the exemplary embodiment the side wall 56 of the receptacle 50 includes an extension 60 that extends into the receptacle 50. In the exemplary embodiment, the stud 40 includes an optional reduced-diameter portion 62. When the stud 40 is received within the receptacle 50, the extension 60 engages the reduced-diameter portion 62 of the stud 40 to hold the stud 40 within the receptacle 50 in a snap-fit connection. In the exemplary embodiment, the extension 60 extends along an entirety of a circumference of the side wall 56 such that the extension 60 defines a reduced-diameter portion 64 of the receptacle 50, relative to the bottom end portion 54. Alternatively, the extension 60 may be one or more extensions that each extend along only a portion of the circumference of the side wall 56. It is noted that although the receptacle 50 and the stud 40 have approximately circular cross sectional shapes in the exemplary embodiment, alternatively the receptacle 50 and/or the stud 40 may have other non-circular cross-sectional shapes.

The electrode lead assembly 12 may optionally include an adhesive layer 66 that covers at least a portion of the termination cap 26. Specifically, the adhesive layer 66 includes a pair of opposite surfaces 67 and 69. The surface 67 includes any suitable adhesive for adhering the adhesive layer 66 to the termination cap 26, such as, but not limited to, a self-adhering and/or pressure sensitive adhesive (PSA), and/or the like. The adhesive layer 66 may also cover and adhere to at least a portion of the side portion 34 of the electrode base 28 to facilitate maintaining the connection between the termination cap 26 and the electrode 20. The adhesive layer 66 may optionally include indicia 68. The indicia 68 may indicate any information, such as, but not limited to, a location on the patient's body where the electrode is desired to be placed and/or the like. In the exemplary embodiment, the adhesive layer 66 includes an optional opening 70 that receives a portion of the body 44 of the termination cap 26.

Figure 4:
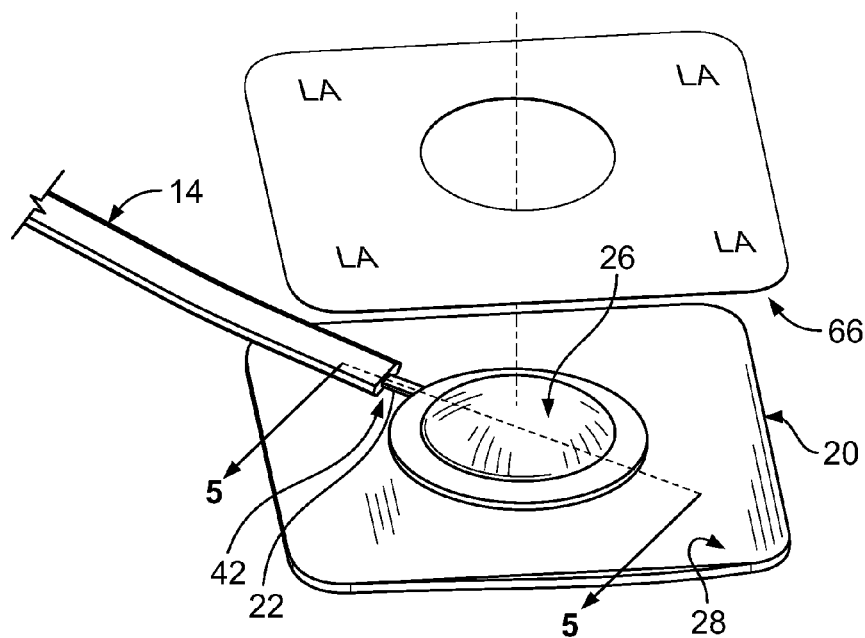
FIG. 4 is a perspective view of the electrode lead assembly shown in FIG. 2 illustrating the electrode lead assembly in an assembled state.
Figure 5:
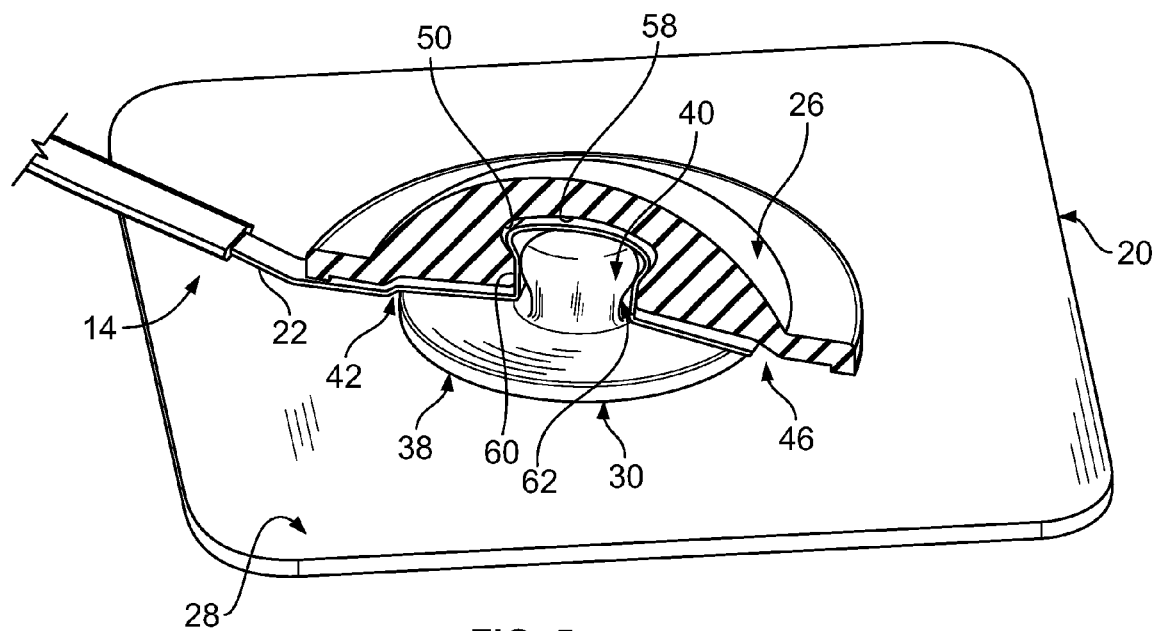
FIG. 5 is a cross sectional view of a portion of the electrode lead assembly shown in FIG. 4 taken along line 5-5 of FIG. 4.

Referring now to FIGS. 4 and 5, to terminate the electrical lead 14 to the electrode 20, the end portion 42 of the electrical conductor 22 is positioned over the stud 40 of the electrode 20. The termination cap 26 is positioned over the stud 40 and moved in a direction toward the electrode 20 such that the stud 40 is received within the receptacle 50 of the termination cap 26. In the exemplary embodiment, a portion of the end portion 42 of the electrical conductor 22 thereby extends between, and is engaged with, the bottom wall 58 of the receptacle 50 and the stud 40 of the electrode 20. The engagement between the stud 40 and the end portion 42 of the electrical conductor 22 forms an electrical connection between the electrode 20 and the electrical conductor 22. Although the end portion 42 of the electrical conductor 22 is engaged with and between the bottom wall 58 of the receptacle 50 and the stud 40 of the electrode 20, the end portion 42 of the electrical conductor 22 may alternatively be engaged with and between any other portion(s) of the termination cap 26 besides the bottom wall 58 and any portion(s) of the stud 40 (whether or not the receptacle 50 extends completely through the body 44), such as, but not limited to, embodiments wherein the end portion 42 of the electrical conductor 22 is engaged with and between the side wall 56 of the termination cap 26 and the stud 40.

As can be seen in FIG. 5, the termination cap 26 may also capture a portion of the end portion 42 of the electrical conductor 22 between the side portion 46 of the termination cap 26 and the end portion 38 of the electrical contact 30 such that the electrical conductor 22 is engaged with, and thereby electrically connected to, the end portion 38 of the electrical contact 30. In the exemplary embodiment, the complimentary size and shape of the receptacle 50 relative to the stud 40 causes a portion of the end portion 42 of the electrical conductor 22 to conform approximately to at least a portion of the contour of the stud 40. Engagement between the extension 60 and the reduced-diameter portion 62 of the stud 40 facilitates holding the termination cap 26 on the electrode 20 in a snap-fit connection.

Once the termination cap 26 is assembled on the electrode 20, the optional adhesive layer 66 (not shown in FIG. 5) may be attached to the termination cap 26 and/or the electrode base 28 as is shown in FIG. 4. As described above, the adhesive layer 66 may facilitate maintaining the connection between the termination cap 26 and the electrode 20. Moreover, the adhesive layer 66 may capture a portion of the electrical lead 14 between the base 28 of the electrode 20 and the adhesive layer 66, which may facilitate providing strain relief to the electrical lead 14.

The electrical leads 14 and the termination caps 26 may be sold or supplied to healthcare providers, or an intermediate party, as part of the electrode lead set 10 or a single electrode lead assembly 12, whether supplied or sold as terminated to the electrodes 20. Alternatively, the electrical leads 14 and the termination caps 26 may be supplied or sold to healthcare providers, or an intermediate party, without the electrodes 20 and the healthcare provider, or the intermediary party, may supply and terminate the electrodes 20 to the electrical leads 14, for example immediately prior to application of the electrodes 20 to the patient's body. Moreover, the termination caps 26 may be sold or supplied to healthcare providers, or an intermediate party, by themselves and the healthcare provider, or the intermediary party, may supply the electrical leads 14 and the electrodes 20. In some embodiments, the electrical leads 14 and/or the termination caps 26 may be reusable with different electrodes 20, for example by removing the termination cap 26 to disconnect the electrical lead 14 from an electrode 20 and terminating the electrical lead 14 to another electrode 20 using the termination cap 26. In other embodiments, once an electrical lead 14 is terminated to an electrode 20, the electrical lead 14 and/or the termination cap 26 is not intended to be reusable with another electrode.

Figure 6:
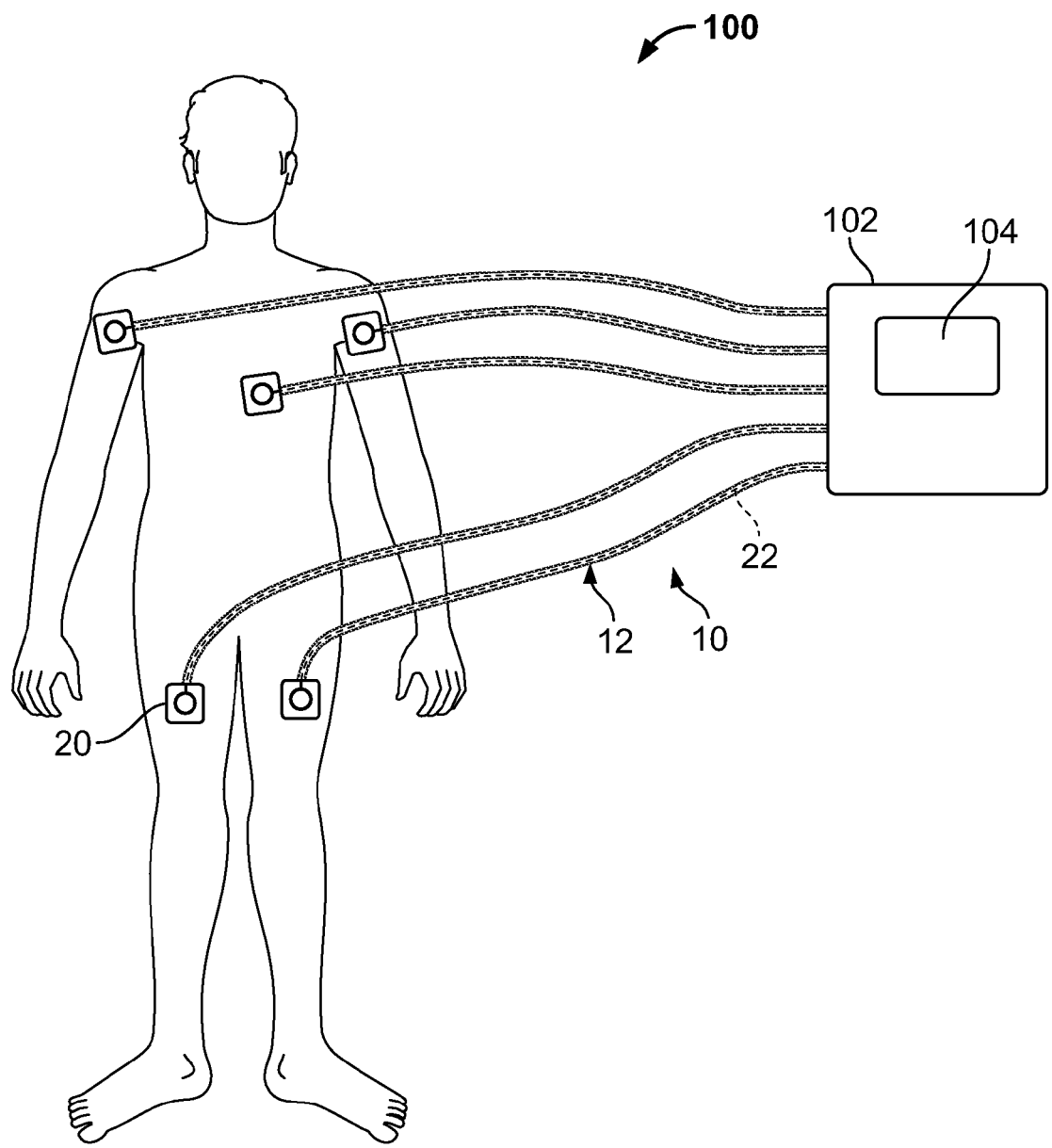

FIG. 6 is a schematic diagram of an exemplary embodiment of an ECG system 100 that the electrode lead set 10 may be, but is not limited to being, used with. The ECG system 100 includes the electrode lead set 10 and an ECG monitoring device 102. The electrode lead set 10 is connected to the ECG monitoring device 102 such that the electrical conductors 22 are electrically connected to one or more corresponding circuits (not shown) of the ECG monitoring device 102. Each electrode lead assembly 12 may directly connect to the ECG monitoring device 102, or may connect to the device 102 using any suitable extension (not shown). The ECG monitoring device 102 may be any suitable processing device that is capable of performing signal processing and computational operations to convert the raw electrical signals from and/or to the electrodes 20 into meaningful ECG information that may optionally be displayed on a monitor 104, printed for review by a physician, and/or the like.

In operation, each electrode lead assembly 12 is manipulated to place the corresponding electrode 20 at a desired location on the patient's body. In the exemplary embodiment of FIG. 6, some of the electrodes 20 are placed on a chest region of the patient's body adjacent the heart, and others of the electrodes 20 are placed on the patient's body at the prescribed limb locations RA, LA, RL, and LL of the AHA. However, the ECG system 100 is not limited to using five electrodes 20, is not limited to the specific locations shown, and each of the electrodes 20 is not limited to being placed at the corresponding location shown. Rather, the ECG system 100 may use any number of electrodes 20 each located at any suitable location on the patient's body for performing ECG measurements. The particular locations shown in FIG. 6 as well as which electrode 20 of the set 10 is placed at such locations is meant as exemplary only. For example, the set 10 may include more or less electrode lead assemblies 12 and electrodes 20 than five, and/or the system 100 may use more than one electrode lead set (e.g., a set for the chest region and a different set for the limbs). Different locations (e.g., different locations on the chest region and/or the limbs) than those shown may be used in addition or alternative to the locations shown.

Once all of the electrodes 20 are placed at the desired locations on the patient's body, the ECG monitoring device 102 receives electrical signals of the electrodes 20 and converts the signals into meaningful ECG information.

In an alternative embodiment, the electrical conductors 22 are electrically connected to a hand-held system monitor (not shown). In another alternative embodiment, the electrical conductors 22 are electrically connected to a wireless transceiver (not shown) such that the ECG signals are transmitted to the hand-held system monitor and/or the ECG monitoring device 102 via a wireless connection.

The embodiments thus described provide an electrical lead that may be less costly and/or more easily manufactured, assembled, and/or terminated to an electrode than at least some known electrical leads.

Although the embodiments described and illustrated herein are described and illustrated herein for use with an ECG system, the embodiments described and illustrated herein are not limited to being used with ECG systems for taking ECG measurements. Rather, the embodiments described and illustrated herein may be used with any system for measuring any physiologic information or performing any physiologic procedure, such as, but not limited to, for performing an electroencephalogram (EEG) procedure, for performing muscle and/or nerve stimulation and/or therapy, and/or for performing an electrophysiologic procedure. In some embodiments, the embodiments described and illustrated herein may be a hybrid that may be used to perform a plurality of different types of physiologic measurements and/or procedures.

Exemplary embodiments are described and/or illustrated herein in detail. The embodiments are not limited to the specific embodiments described herein, but rather, components and/or steps of each embodiment may be utilized independently and separately from other components and/or steps described herein. Each component, and/or each step of one embodiment, can also be used in combination with other components and/or steps of other embodiments. When introducing elements/components/etc. described and/or illustrated herein, the articles "a", "an", "the", "said", and "at least one" are intended to mean that there are one or more of the element(s)/component(s)/etc. The terms "comprising", "including" and "having" are intended to be inclusive and mean that there may be additional element(s)/component(s)/etc. other than the listed element(s)/component(s)/etc. Moreover, the terms "first," "second," and "third," etc. in the claims are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

While the subject matter described and illustrated herein has been described in terms of various specific embodiments, those skilled in the art will recognize that the subject matter described and illustrated herein can be practiced with modification within the spirit and scope of the claims.

What is claimed is:

1. A termination cap for terminating an electrical lead comprising an electrical conductor to a stud of an electrode, said termination cap comprising:
   a body; and
   a receptacle extending into the body, the receptacle comprising a size and shape that is complimentary to the stud of the electrode such that the receptacle is configured to receive at least a portion of the stud therein, wherein the receptacle is configured such that when the stud is received within the receptacle, the receptacle is configured to hold a portion of the electrical conductor between the body and the stud such that the electrical conductor is engaged with and electrically connected to the stud.

2. The termination cap according to claim 1, wherein the receptacle extends within the body between an open end portion and a bottom end portion, the bottom end portion having a bottom wall, the receptacle being configured to hold a portion of the electrical conductor between the bottom wall and the stud.

3. The termination cap according to claim 1, the receptacle is partially defined by a side wall, a portion of the side wall comprising an extension extending into the receptacle.

4. The termination cap according to claim 1, wherein at least a portion of the receptacle has a reduced diameter relative to another portion of the receptacle, the reduced diameter portion of the receptacle being configured to engage a reduced diameter portion of the stud when the stud is received within the receptacle.

5. The termination cap according to claim 1, further comprising an adhesive layer configured to cover at least a portion of the termination cap.

6. The termination cap according to claim 1, further comprising an adhesive layer configured to cover at least a portion of the termination cap, wherein the adhesive layer comprises indicia.

7. The termination cap according to claim 1, wherein the termination cap is configured to connect to the stud using a snap-fit connection.

8. The termination cap according to claim 1, wherein the complimentary size and shape of the receptacle relative to the stud causes a portion of the electrical conductor to conform approximately to the contour of at least a portion of the stud when the stud is received within the receptacle.

9. An electrode lead assembly comprising:
   a termination cap including a body and a receptacle extending into the body;
   an electrode comprising a stud, at least a portion of the stud being received within the receptacle, the receptacle comprising a size and shape complimentary to the stud of the electrode; and
   an electrical lead comprising an electrical conductor, a portion of the electrical lead extending within the receptacle between the stud and the body of the termination cap such that the electrical conductor is engaged with and electrically connected to the stud.

10. The electrode lead assembly according to claim 9, wherein the receptacle extends into the body between an open end portion and a bottom end portion, at least a portion of the receptacle having a reduced diameter relative to the bottom end portion.

11. The electrode lead assembly according to claim 9, wherein the receptacle is at least partially defined by a wall of the body, the wall comprising an extension extending into the receptacle, the extension engaging a reduced diameter portion of the stud.

12. The electrode lead assembly according to claim 9, further comprising an adhesive layer covering at least a portion of the termination cap.

13. The electrode lead assembly according to claim 9, further comprising an adhesive layer covering at least a portion of the termination cap, wherein the adhesive layer comprises indicia.

14. The electrode lead assembly according to claim 9, wherein the portion of the electrical conductor that extends within the receptacle is an end portion of the electrical lead.

15. The electrode lead assembly according to claim 9, wherein the termination cap is connected to the stud using a snap-fit connection.

16. The electrode lead assembly according to claim 9, wherein the electrical conductor comprises one of an approximately cylindrical wire and an approximately planar shape.

17. The electrode lead assembly according to claim 9, wherein the electrical lead extends between a distal end portion where a portion of the electrical conductor is electrically connected to the stud and a proximal end portion that is configured to be electrically connected to an electronic device.

18. The electrode lead assembly according to claim 9, wherein the receptacle has a complimentary size and shape relative to the stud such that the portion of the electrical conductor that extends within the receptacle conforms approximately to the contour of at least a portion of the stud.

19. The electrode lead assembly according to claim 9, wherein the electrode lead assembly is an electrocardiograph (ECG) electrode lead assembly.

20. An electrical lead assembly for termination to a stud of an electrode, said electrical lead assembly comprising:
   an electrical lead comprising an electrical conductor; and
   a termination cap comprising a body and a receptacle extending into the body, the receptacle comprising a size and shape that is complimentary to the stud of the electrode such that the receptacle is configured to receive at least a portion of the stud therein, wherein the receptacle is configured such that when the stud is received within the receptacle, the receptacle is configured to hold a portion of the electrical conductor between the body and the stud such that the electrical conductor is engaged with and electrically connected to the stud.

* * * * *